United States Patent [19]
Philips et al.

[11] Patent Number: 6,019,783
[45] Date of Patent: Feb. 1, 2000

[54] COOLING SYSTEM FOR THERAPEUTIC CATHETER

[75] Inventors: Peter J. Philips, Trabuco Canyon; Wayne Arthur Noda, Mission Viejo, both of Calif.

[73] Assignee: Alsius Corporation, Irvine, Calif.

[21] Appl. No.: 09/260,950

[22] Filed: Mar. 2, 1999

[51] Int. Cl.[7] .................................. A61F 7/00
[52] U.S. Cl. ....................... 607/105; 607/104; 606/21
[58] Field of Search .................. 607/104, 105, 607/113, 96, 98; 606/20, 21, 22, 23, 24

[56] References Cited

U.S. PATENT DOCUMENTS

| | | | |
|---|---|---|---|
| 4,281,516 | 8/1981 | Berthet et al. | 62/3 |
| 4,759,349 | 7/1988 | Betz et al. | 128/6 |
| 4,919,134 | 4/1990 | Streeter | 128/400 |
| 4,962,761 | 10/1990 | Golden | 607/104 |
| 5,139,496 | 8/1992 | Hed | 606/23 |
| 5,174,285 | 12/1992 | Fontenot | 128/400 |
| 5,269,758 | 12/1993 | Taheri | 604/96 |
| 5,344,436 | 9/1994 | Fontenot et al. | 607/104 |
| 5,452,582 | 9/1995 | Longsworth | 62/51.2 |
| 5,514,094 | 5/1996 | Anello et al. | 604/113 |
| 5,545,161 | 8/1996 | Imran | 606/41 |
| 5,624,392 | 4/1997 | Saab | 604/43 |
| 5,733,319 | 3/1998 | Neilson et al. | 607/105 |
| 5,787,715 | 8/1998 | Dobak, III et al. | 62/51.2 |
| 5,871,526 | 2/1999 | Gibbs et al. | 607/104 |
| 5,879,329 | 3/1999 | Ginsburg . | |

*Primary Examiner*—Linda C. M. Dvorak
*Assistant Examiner*—Roy Gibson
*Attorney, Agent, or Firm*—John L. Rogitz

[57] ABSTRACT

A heat exchanger to remove heat from coolant in a closed circuit cooling catheter includes two heat exchange stages. Each stage includes a heat exchange element, such as a group of hollow fibers, and a TEC array juxtaposed with the heat exchange element to remove heat from the element. The elements are in fluid series with each other and are separated from each other by a thermal barrier. A thermal interface can be provided between each element and its TEC array. In one embodiment, the thermal interface is a gel layer. In another embodiment, the thermal interface is an ethylene glycol bath.

19 Claims, 4 Drawing Sheets

COOLING SYSTEM FOR THERAPEUTIC CATHETER

FIELD OF THE INVENTION

The present invention relates generally to methods and apparatus for heating and cooling patients for therapeutic purposes, and more particularly to systems for treating brain trauma and brain ischemia by inducing hypothermia in a patient.

BACKGROUND

It has been discovered that the medical outcome for a patient suffering from severe brain trauma or from ischemia caused by stroke or heart attack is degraded if the patient's body temperature rises above normal (38° C.). It is further believed that the medical outcome for many such patients might be significantly improved if the patients were to be cooled relatively quickly to around 32° C. for a short period, e.g., 24–72 hours.

The affected organ, in any case, is the brain. Accordingly, systems and methods have been disclosed that propose cooling blood flowing to the brain through the carotid artery. An example of such systems and methods is disclosed in co-pending U.S. pat. app. Ser. No. 09/063,984, filed Apr. 21, 1998, owned by the present assignee and incorporated herein by reference. In the referenced application, various catheters are disclosed which can be advanced into a patient's carotid artery and through which coolant can be pumped in a closed circuit, to remove heat from the blood in the carotid artery and thereby cool the brain. The referenced devices have the advantage over other methods of cooling (e.g., wrapping patients in cold blankets) of being controllable, relatively easy to use, and of being capable of rapidly cooling and maintaining blood temperature at a desired set point.

As recognized in co-pending U.S. pat. app. Ser. No. 09/133,813, filed Aug. 13, 1998, owned by the present assignee and incorporated herein by reference, the above-mentioned advantages in treating brain trauma/ischemic patients by cooling can also be realized by cooling the patient's entire body, i.e., by inducing systemic hypothermia. The advantage of systemic hypothermia is that, as recognized by the present assignee, to induce systemic hypothermia a cooling catheter or other cooling device need not be advanced into the blood supply of the brain, but rather can be easily and quickly placed into the relatively large vena cava of the central venous system. Moreover, since many patients already are intubated with central venous catheters for other clinically approved purposes anyway, providing a central venous catheter that can also cool the blood requires no additional surgical procedures for those patients.

Regardless of where the cooling occurs, however, it is clear that heat must be removed from the coolant that flows through the catheter. As recognized herein, it is desirable that a cooling system for a cooling catheter consume minimal energy and space. Small size is desired because space is often at a premium in critical care units. Moreover, as also recognized herein, for patient comfort it is desirable that such a cooling system generate a minimum amount of noise. As still further understood by the present invention, it is desirable that the cooling system be easy to use by health care personnel, and that the portion of the cooling system that directly contacts the catheter coolant be disposable. We understand that if the portion of the cooling system that directly contacts the catheter coolant were not disposable, the portion undesirably would require sterilization by, e.g., autoclaving prior to reuse, because even though the coolant does not directly contact the patient but is instead contained within the catheter, the potential arises that through in-leakage or other means body fluid might indeed contaminate the coolant. Accordingly, it is the object of the present invention to address one or more of the above-noted considerations.

SUMMARY OF THE INVENTION

A heat exchange system for a catheter includes at least one heat exchange element that is connectable to the catheter for receiving coolant from the catheter, and at least one thermal electric cooler (TEC) in thermal contact with the heat exchange element for heating or cooling the element such that coolant is returned to catheter to heat or cool the catheter.

In a preferred embodiment, the heat exchange element is plastic. More preferably, the heat exchange element includes plural hollow fibers, or, the heat exchange element can include at least one non-linear plastic tube. As another alternative, the heat exchange element can include a bag that has plural fluid paths through the bag which are established by, e.g., heat-staking portions of the bag together. A thermal interface such as an aluminum oxide gel or metallized plastic foil bag can be sandwiched between the heat exchange element and the TEC to removably couple the element to the TEC. Less desirably, the heat exchange element includes at least one metal tube in thermal contact with the TEC. For cooling efficiency, two cooling stages can be used, with each cooling stage including a respective heat exchange element with associated TEC assembly, and at least one thermal barrier is disposed between the elements.

In another embodiment, a heat exchange fluid is disposed between the TEC and the heat exchange element such that the heat exchange element is disposed in the fluid. The fluid can be cold ethylene glycol. An agitator is disposed in the fluid to move the fluid.

In another aspect, a cooling system for a therapeutic medical device includes at least one heat exchanger made at least partially of plastic. The heat exchanger receives coolant from the medical device and returns coolant thereto. A thermal electric cooler (TEC) is in thermal contact with the heat exchanger for removing heat from the heat exchanger.

In still another aspect, a cooling system includes catheter means for conveying coolant into a patient's body without directly contacting the coolant with the body. Also, the system includes heat exchanger means communicating with the catheter means for receiving coolant therefrom and returning coolant thereto. Cooling means is in thermal contact with the heat exchanger means for conveying heat away from the heat exchanger means.

In yet another aspect, a controller is disclosed for establishing a control signal for controlling coolant temperature in a therapeutic catheter cooling system. The cooling system can include a coolant pump and at least one TEC, and the controller includes logic means that receive a desired patient temperature and a measured patient temperature. The controller logic determines a control signal in response to the temperatures, with the control signal being sent to the cooling system for establishing the coolant temperature. Preferably, the control signal is also established in accordance with a measured patient temperature time derivative and/or time integral. As intended by the present invention, the control signal is used to establish at least one of: a speed of the coolant pump, and an energization of the TEC.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
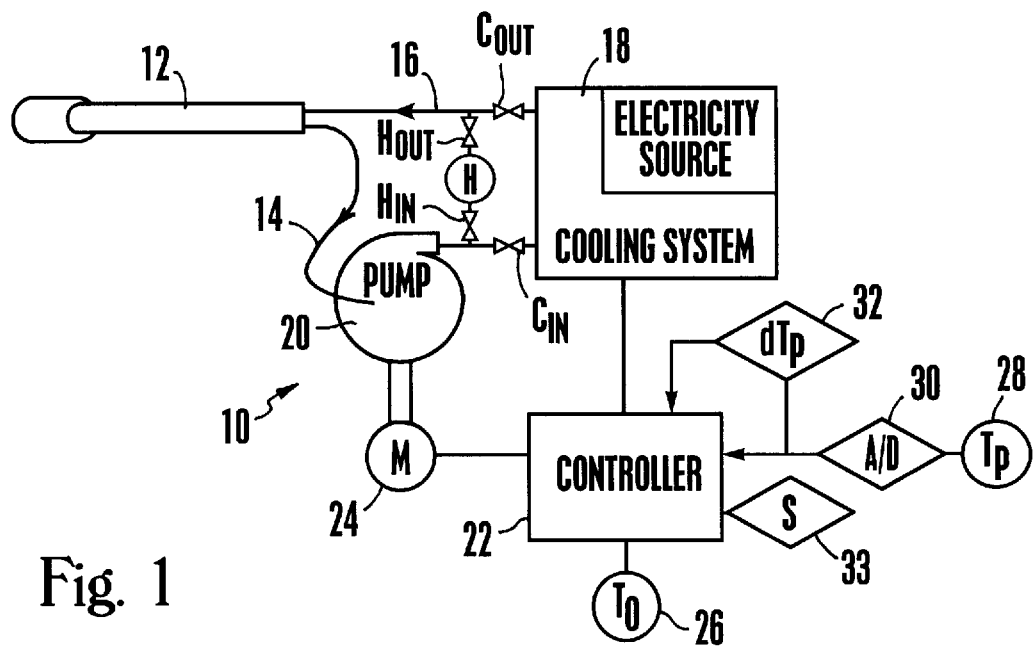
FIG. 1 is a schematic view of the cooling system in its intended environment.

Referring initially to FIG. 1, a cooling system, generally designated 10, for a therapeutic catheter 12 is shown. In the preferred embodiment, the catheter 12 is a cooling catheter that can be advanced into a patient's carotid artery or, more preferably, vena cava, to cool the patient (and, when it is desired to warm the patient back up, to heat the patient) to thereby improve the medical outcome for the patient when the patient has suffered from severe brain trauma or ischemia. Preferred catheters are disclosed in the above-referenced patent applications. Less preferred catheters are disclosed in U.S. Pat. Nos. 5,411,477 and 5,342,301 to Saab and U.S. Pat. No. 5,837,003 owned by Radiant Medical. While referred to herein as a "cooling system", it is to be understood that the system 10 more generally is a heat exchange system that preferably removes heat from the catheter 12 but that can also add heat thereto if necessary to correct "overshoot" of patient temperature and warm the patient after cooling therapy.

As shown, the system 10 receives coolant from the catheter 12 via a coolant return line 14, and the system 10 supplies coolant to the catheter 12 via a coolant supply line 16. Thus, the catheter 12 is a closed circuit cooling system through which coolant is circulated to remove heat from the patient, with the coolant being cooled or heated by the system 10 as more fully disclosed below. As set forth in the above-referenced patent applications, the coolant preferably is a biocompatible liquid, such as saline. If desired, however, non-biocompatible fluids can be used to achieve lower coolant temperatures than is otherwise available with saline.

The coolants lines 14, 16 can be IV lines or tubes or other suitable fluid conduits, such as metal (steel) tubes. When the coolant lines 14, 16 are plastic tubes, they can be connected to the catheter 12 and the system 10 by suitable connecting structure, such as Luer fittings, interference fits, solvent bonding, heat staking, ultrasonic welding, and the like.

FIG. 1 shows that the cooling system 10 includes a heat exchanger 18 (disclosed further below), a pump 20, and, if desired, a controller 22. Preferably, the pump 20 is a peristaltic pump, but other types of positive displacement pumps, such as but not limited to piston pumps and roller pumps, or even centrifugal pumps, can be used. A peristaltic pump is preferred in the present implementation because it can pump coolant without directly contacting the coolant, but instead simply by squeezing a tube through which the coolant flows. In this way, the pump 20 is reusable, and only the catheter 12 and portions of the system 10 coming in direct contact with the coolant need be made disposable to render an advantageously disposable system.

As shown, the pump 20 takes a suction on the coolant return line 14 and discharges coolant to the heat exchanger 18, from whence the coolant passes back to the catheter 12 via the coolant supply line 16. It is to be understood, however, that the pump 20 could be disposed on the discharge side of the heat exchanger 18, if desired.

As further shown, the pump 20 includes an electric or other type of motor 24, and the controller 22 can be electrically connected to the motor 24 to control the rate at which coolant is pumped by the pump 20. Also, the controller 22 can be electrically connected to elements in the heat exchanger 18 to control the rate at which heat is added or subtracted from the coolant. As more fully set forth below, the controller 22 can be implemented by a software-executing processor or by discrete logic circuits or other electronic circuitry device to establish a desired patient temperature by appropriately controlling the pump 20 and/or heat exchanger 18.

As intended by the present invention, the desired patient temperature $T_0$ can be input by means of a rheostat or keyboard or other input device 26, or it can be preprogrammed into the controller 22. In any case, the controller 22 receives a temperature signal $T_P$ from one or more temperature sensors 28, with the temperature signals having been digitized by means of an analog to digital converter 30 and processed if desired by a differentiator 32 and integrator 33, such that the controller can, if desired, receive a temperature signal, a signal representing the time rate of change of patient temperature and a signal representing the time integral of temperature, for purposes to be shortly disclosed. It is to be understood that the temperature sensor 28 can be a thermistor, thermocouple, RTD, or other temperature sensing element that can be orally or rectally placed in the patient or that can be mounted on the catheter 12 or otherwise associated with the patient (e.g., the sensor 28 can be an infrared device) to detect a temperature of the patient.

If desired, a heater "H" can be provided to heat coolant that has become too cold. When a heater is provided, heater inlet and outlet valves $H_{in}$, $H_{out}$ can be opened to permit coolant to flow through the heater. Under these conditions, coolant inlet and outlet valves $C_{in}$, $C_{out}$ can be provided at the inlet and outlet of the cooling system 18 and can be shut, to prevent coolant from entering the cooling system 18. It will readily be appreciated that under normal conditions, it is desired to remove heat from the coolant, in which case the heater inlet and outlet valves $H_{in}$, $H_{out}$ are shut and the coolant inlet and outlet valves $C_{in}$, $C_{out}$ are open. The valves can be manually controlled or, more preferably, are solenoid controlled, with the valve solenoids being electrically connected to the controller 22 for control thereby. Likewise, the heater "H" is controlled by the controller 22. Alternatively, no heater (and, hence, no heater inlet and outlet valves) need be provided. Instead, the TEC elements of the present invention can be reversed to become warm instead of cool by reversing current flow through them, when it is desired to heat the coolant.

Figure 2:
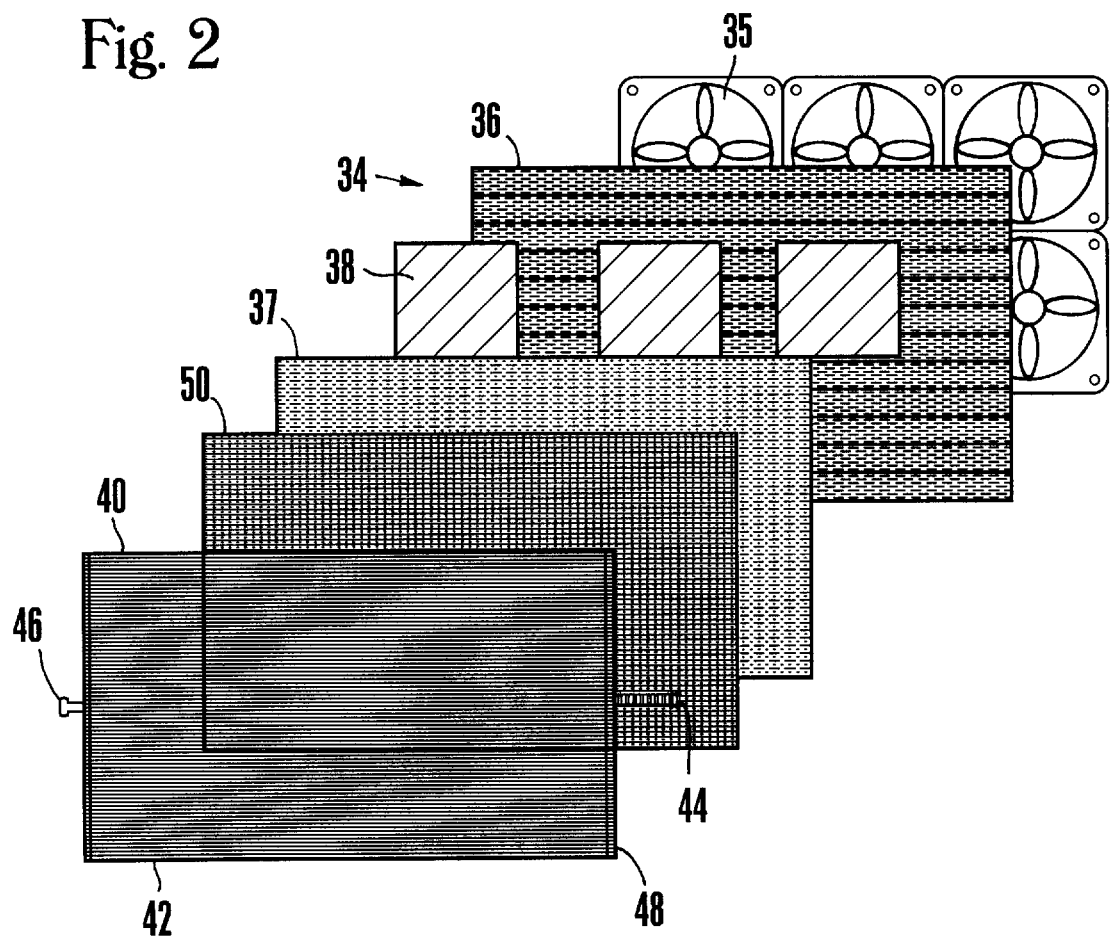
FIG. 2 is an exploded perspective view of one of two cooling stages of the present system.
Figure 3:
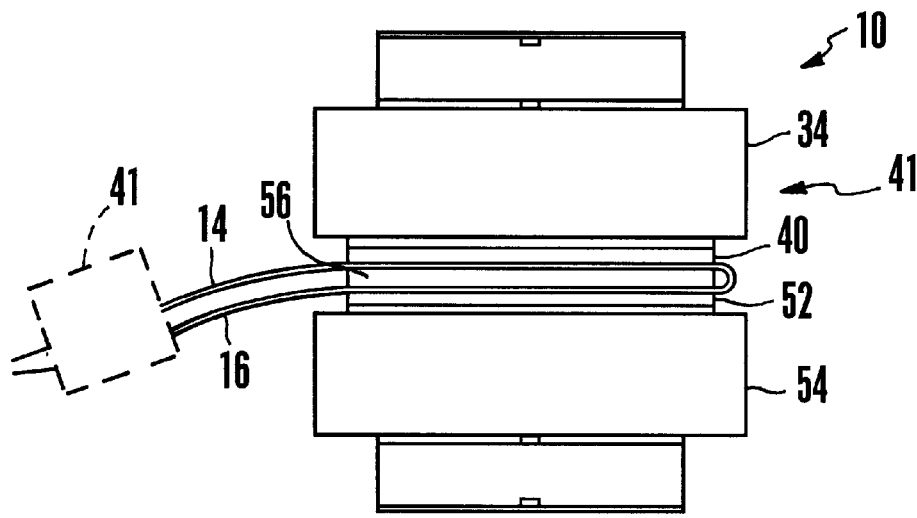
FIG. 3 is a schematic top view of the cooling system, showing both cooling stages.

FIGS. 2 and 3 show the details of one preferred heat exchanger 18. As shown, a first thermoelectric cooler (TEC) assembly 34 includes at least one heat sink 36 from which heat can be removed by an array of fans 35. Also, the first TEC assembly 34 includes at least one cold plate 37 in thermal contact with the heat sink 36, and plural TEC elements 38 are sandwiched between the cold plate 37 and heat sink 36 in accordance with TEC principles known in the art. As known in the TEC art, the TEC elements 38 are connected to source of electricity to cause the temperature of the elements to change, and more particularly to cool the cold plate 37, with heat being removed from the TEC elements 38 by the heat sink 36. The TEC assembly 34 can be purchased from TE Technology of Traverse City, Mich.

A first heat exchange element 40 is positioned against the cold plate 37 as shown. Preferably, the heat exchange element 40 is disposable. In one embodiment, the heat exchange element 40 is made of plastic, and more preferably is made of plural co-parallel thin-walled hollow fibers 42 that have inlet ends communicating with a coolant return line fitting 44 that in turn is connected to the coolant return line 14. Also, the fibers 42 have outlet ends communicating with a coolant supply fitting 46 that in turn is connected to the coolant supply line 16. The fibers 42 can be held in a disposable plastic bag or other container 48 for convenience, with the fibers 42 thus defining plural fluid paths through the bag. It is to be understood that the catheter 12, coolant lines 14, 16, and heat exchange element 40 can be provided as an integrated disposable product, with one of the lines 14, 16 being engaged with the pump 20 and with the bag or container 48 being disposed next to the cold plate 37 when it is desired to use the catheter 12 to cool a patient.

If desired, a layer or sheet 50 of aluminum oxide gel or mylar or metallized plastic foil or other thermal interface material can be sandwiched between the bag or container 48 and the cold plate 37. For example, a layer of gel made by Raychem can be provided with paper protective layers on each face of the layer, and then the paper peeled away and the gel applied to the bag or container 48 when it is desired to engage the bag or container 48 with the cold plate 37. Then, the bag or container 48 with layer or sheet 50 is pressed, thermal interface first, against the cold plate 37 to hold the bag or container 48 against the cold plate 37.

Although a single heat exchange element 40 with TEC assembly 34 can be used, more preferably at least two heat exchange elements with respective TEC assemblies are used to establish a dual-element assembly 41, as shown in FIG. 3, to effect comparatively efficient staged cooling. As shown, the first heat exchange element 40 is in fluid series with a second heat exchange element 52, which in turn is closely juxtaposed with a second TEC assembly 54, such that coolant first passes through the first element 40 to be cooled therein, and then passes through the second heat exchange element 52 for further cooling. It is to be understood that the heat exchange elements 40, 52 can be identical to each other in structure and operation, and that the heat exchange assemblies 34, 54 likewise can be identical to each other in structure and operation. A thermal barrier 56 can be disposed between the heat exchange elements 40, 52 as shown, if desired. The thermal barrier 56 can be a relatively thick block of thermal insulating foam or other insulative material. Additionally, more than one dual element assembly 41 can be used. Indeed, as shown in FIG. 3 two or more dual element assemblies 41 can be used in series. Or, if desired the coolant return and supply lines 14,16 can be established by two lines each with each set of lines being cooled in parallel with the other set by engaging each set in respective dual element assemblies 14 that are arranged in parallel with each other.

Figure 4:
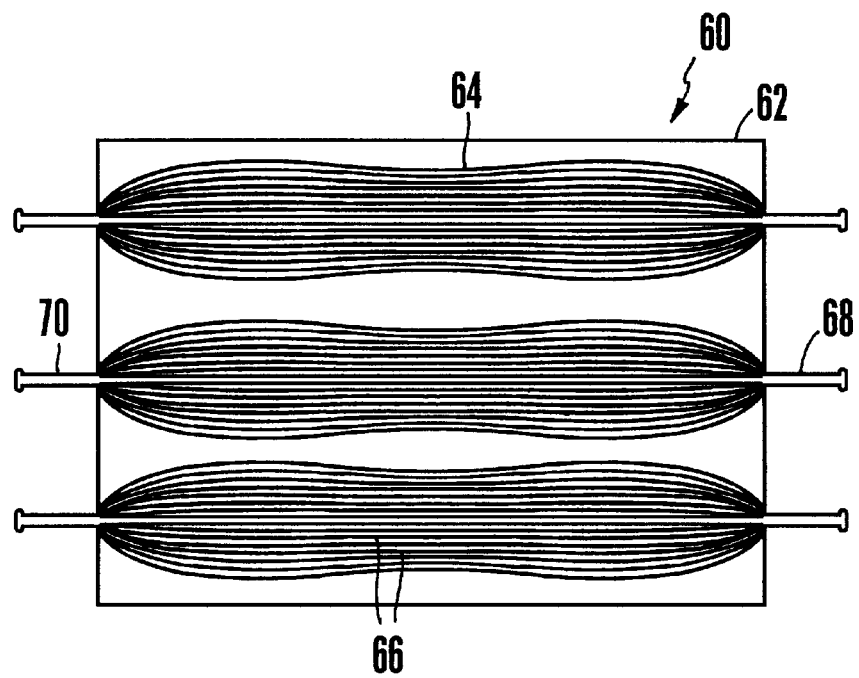
FIG. 4 is a side view of an alternate cooling element.

FIG. 4 shows an alternative heat exchange element, generally designated 60, which includes a plastic frame 62 that supports plural bundles 64 of hollow fibers 66. Each bundle 64 can include an inlet fitting 68 and an outlet fitting 70 for communicating cold fluid to the catheter 12 (FIG. 1). If desired, the frame can be made of metal or ceramic or other material, but is preferably plastic to promote disposability.

Figure 5:
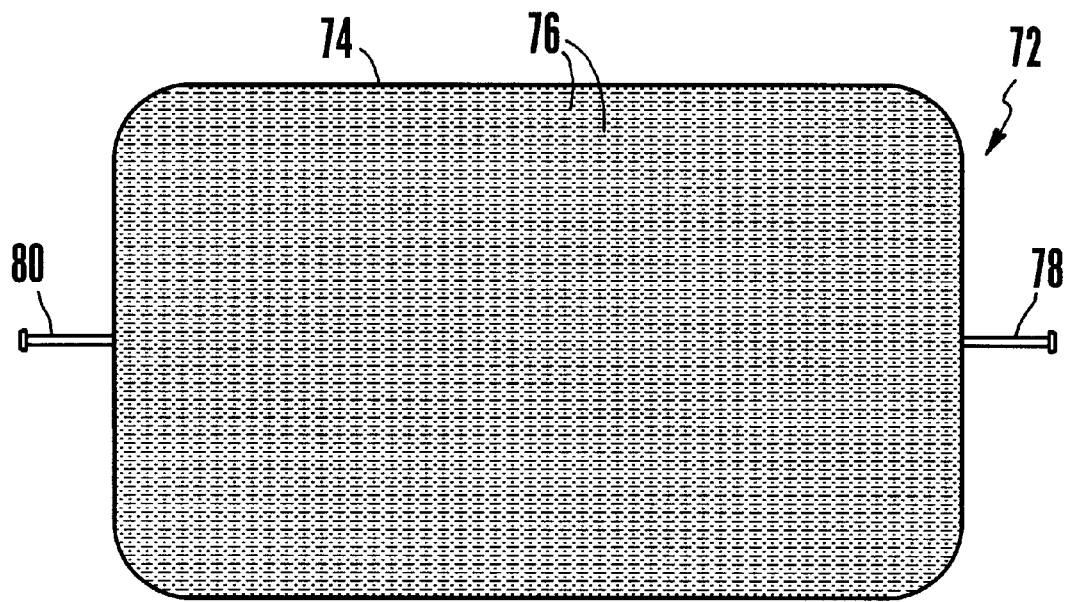
FIG. 5 is a side view of another alternate cooling element.

FIG. 5 shows yet another alternative heat exchange element, generally designated 72, which includes a foil or plastic bag 74 that has been heat-staked along multiple locations to create a long fluid path 76 with a length that is greater than the dimension of the element 72 itself. The fluid path 76 communicates with an inlet fitting 78 and an outlet fitting 80 for communicating cold fluid to the catheter 12 (FIG. 1).

Figure 6:
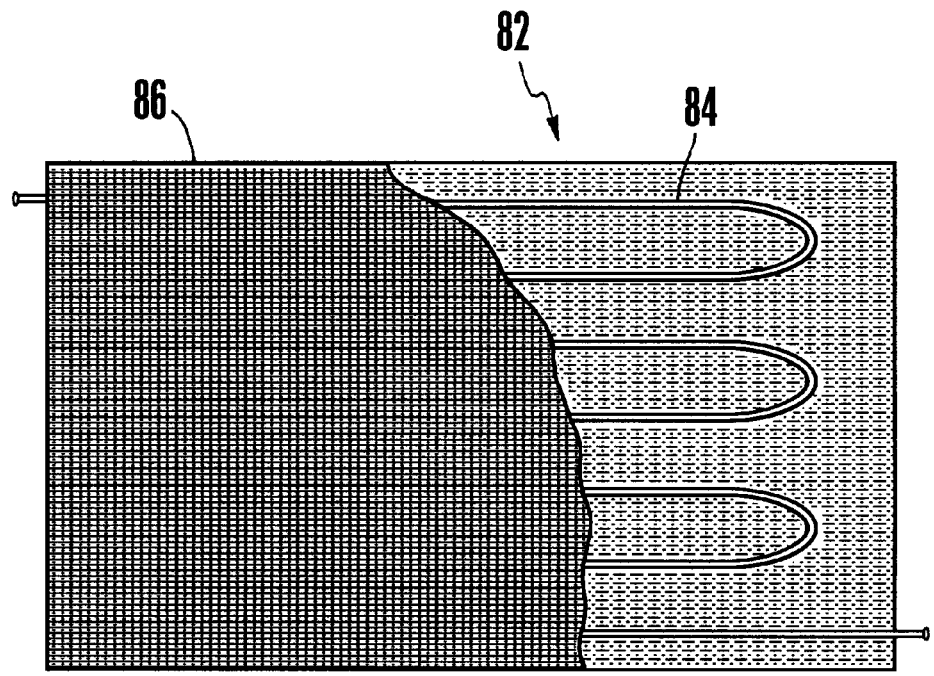
FIG. 6 is a side view of yet another alternate cooling element, with portions of the aluminum casting cut away for clarity.

A still further embodiment of the present heat exchange element is shown in FIG. 6, which shows a heat exchange element 82 having plural copper or steel fluid segments 84 embedded in a metal (e.g., aluminum) casting 86. It is to be understood that the fluid segments 84 can be established by a single steel tube that is configured as shown and that communicates with the return and supply lines 14, 16 shown in FIG. 1.

Figure 7:
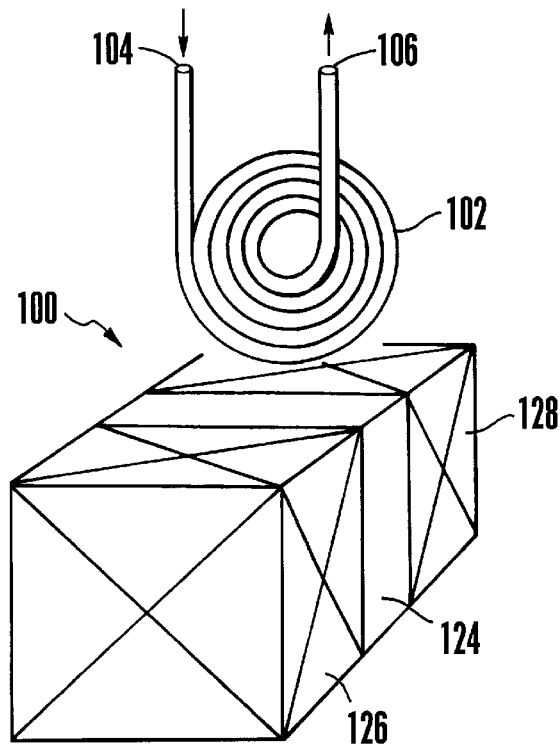
FIG. 7 is an exploded perspective view of one cooling stage of an alternate embodiment of the present system, which uses an ethylene glycol bath.
Figure 8:
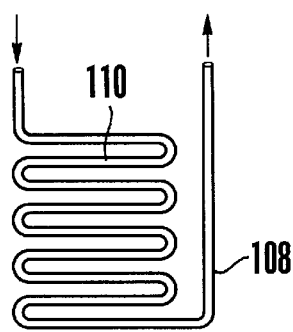
FIG. 8 is a side view of an alternate cooling element for the system shown in FIG. 7.
Figure 9:
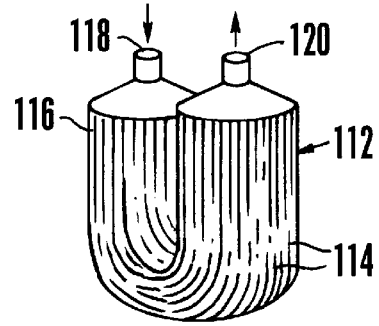
FIG. 9 is a perspective view of another alternate cooling element for the system shown in FIG. 7.

FIGS. 7–10 show an alternate cooling system, generally designated 100, which includes at least one heat exchange element 102 that has an inlet 104 for receiving coolant from the coolant return line 14 (FIG. 1) and an outlet 106 for communicating coolant to the coolant supply line 16, or to a second stage heat exchange element as more fully disclosed below. In the embodiment shown in FIG. 7, the heat exchange element 102 is configured as a coiled metal or plastic (e.g., PVC) tube. In accordance with the present invention, however, a heat exchange element 108 shown in FIG. 8 can replace the element 102 shown in FIG. 7. As shown, the heat exchange element 108 shown in FIG. 8 is a non-linear metal or plastic tube, and more particularly is configured as a continuous series of flattened "S"-shaped segments 110. FIG. 9 shows that as yet another alternative, a heat exchange element 112 can include a bundle of hollow fibers 114 that are held in a bag or other container 116 and that communicate with a fluid inlet port and outlet port 118,120.

Figure 10:
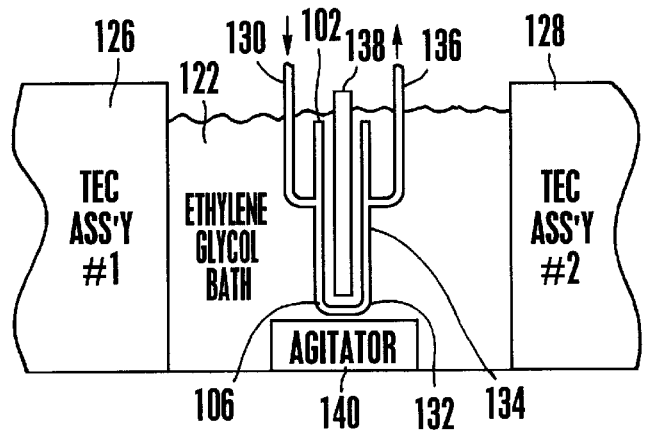
FIG. 10 is a schematic side view of the cooling system shown in FIG. 7.

Regardless of which element is used and taking the element 102 shown in FIGS. 7 and 10 as an example, the element 102 is immersed in a heat exchange bath 122 (FIG. 10) that is held in a bath chamber 124 (FIG. 7). In one preferred embodiment, the fluid in the bath 122 is ethylene glycol liquid. Alternatively, the fluid could be an ice bath, liquid nitrogen, or some other appropriate cold substance.

At least one TEC assembly 126 cools the bath 122. More preferably, the bath 122 is disposed between two TEC assemblies 126, 128, such that the bath 122 is cooled by the assemblies 126, 128. As was the case with the system 10, the system 100 preferably uses two cooling stages. Accordingly, a coolant inlet line 130 interconnects the heat exchange element 102 with the coolant return line 14 (FIG. 1), and the outlet 106 of the heat exchange element 102 is connected to or made integrally with an inlet 132 of a second heat exchange element 134 that is in all essential respects identical to the first heat exchange element 102. After passing through the second exchange element 134, the coolant flows through an outlet line 136 to the coolant supply line 16 (FIG. 1). Preferably, a thermal barrier 138 is disposed between the two cooling stages as shown, and an agitator 140 is disposed in the bath 122 to move the fluid therein. The agitator 140 can be a rotating magnet or rotating vane or other suitable agitator.

Figure 11:
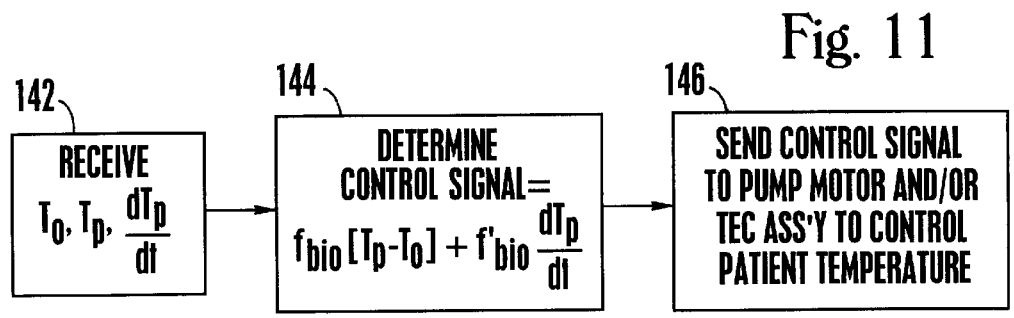
FIG. 11 is a flow chart of the control logic.

FIG. 11 shows the logic by which the controller 22 can control the speed of the pump 20 and/or the electrical current to the present TECs to thereby establish a desired patient temperature. At block 142, the controller receives the desired patient temperature $T_0$ from the input device 26 or from preprogrammed logic. Also, the controller 22 receives the patient temperature signal $T_P$ from the temperature sensor 28. Moreover, in the preferred embodiment the controller 22 receives the time derivative $dT_P/dt$ of the temperature signal $T_P$ and the time integral $\int Tdt$ of the temperature signal $T_P$.

Moving to block 144, the controller determines a control signal by multiplying the difference between the patient temperature signal $T_P$ and the desired patient temperature $T_0$ by a biofunction $f_{bio}$, and then subtracting from this term the product of a derivative biofunction $f'_{bio}$ and the time derivative $dT_P/dt$ of the temperature signal $T_P$. Likewise, the time integral of temperature can be included as a term. The biofunctions $f_{bio}$ and $f'_{bio}$ are empirically determined and can be constants. With the above expression for the control signal in mind, it will be appreciated that the magnitude of the signal will be large and its sign positive when patient temperature is high and rising. In contrast, the magnitude of the signal will be relatively small when patient temperature approaches the desired temperature and/or when the time rate of change of patient temperature is large and negative, to thereby ameliorate the risk of overshoot. Accordingly, when the control signal is positive, additional cooling is indicated, with the magnitude of the control signal being proportional to how much heat per unit time is removed from the coolant by appropriately controlling coolant flow rate (by means of controlling the speed of the pump 20) and/or by appropriately controlling coolant thermal flux (by means of controlling the TECs). The control step is indicated at block 146 in FIG. 11. In the case wherein the control signal is negative (indicated that patient temperature is below desired temperature and/or that the time gradient of coolant temperature is too negative), cooling can be stopped and, when provided, heating commenced by opening the heater inlet and outlet valves $H_{in}$, $H_{out}$, shutting the coolant inlet and outlet valves $C_{in}$, $C_{out}$, and energizing the heater "H".

While the particular COOLING SYSTEM FOR THERAPEUTIC CATHETER as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for".

What is claimed is:

1. A heat exchange system for a catheter, comprising:
   at least one heat exchange element connectable to the catheter for receiving coolant from the catheter; and
   at least one thermal electric cooler (TEC) in thermal contact with the heat exchange element for heating or cooling the element such that coolant is returned to catheter to heat or cool the catheter, wherein the heat exchange element includes plural hollow fibers.

2. The system of claim 1, further comprising an interface sandwiched between the heat exchange element and the TEC to removably couple the element to the TEC.

3. The system of claim 1, further comprising at least one thermal interface between the heat exchange element and the TEC cooler.

4. The system of claim 1, in combination with the catheter.

5. The system of claim 1, further comprising a heater connectable to the catheter to heat coolant.

6. A heat exchange system for a catheter, comprising:
   at least one heat exchange element connectable to the catheter for receiving coolant from the catheter; and
   at least one thermal electric cooler (TEC) in thermal contact with the heat exchange element for heating or cooling the element such that coolant is returned to catheter to heat or cool the catheter, wherein the heat exchange element includes a bag having plural fluid paths through the bag.

7. A heat exchange system for a catheter, comprising:
   at least one heat exchange element connectable to the catheter for receiving coolant from the catheter;
   at least one thermal electric cooler (TEC) in thermal contact with the heat exchange element for heating or cooling the element such that coolant is returned to catheter to heat or cool the catheter; and
   at least first and second heat exchange elements in series and first and second TEC assemblies, each heat exchange element being associated with a respective TEC assembly.

8. The system of claim 7, further comprising at least one thermal barrier between the elements.

9. A cooling system for a therapeutic medical device, comprising:
   at least one heat exchanger made at least partially of plastic, the heat exchanger receiving coolant from the medical device and returning coolant thereto; and
   a thermal electric cooler (TEC) in thermal contact with the heat exchanger for removing heat from the heat exchanger, wherein the heat exchanger includes plural hollow fibers.

10. A cooling system for a therapeutic medical device, comprising:
    at least one heat exchanger made at least partially of plastic, the heat exchanger receiving coolant from the medical device and returning coolant thereto; and
    a thermal electric cooler (TEC) in thermal contact with the heat exchanger for removing heat from the heat exchanger, wherein the heat exchanger includes a bag having plural fluid paths through the bag.

11. The system of claim 10, further comprising an interface sandwiched between the heat exchanger and the TEC to removably couple the element to the TEC.

12. The system of claim 10, further comprising at least one thermal interface between the heat exchanger and the TEC cooler.

13. The system of claim 10, wherein the device is a catheter, and the system is in combination with the catheter.

14. The system of claim 10, further comprising a heater connectable to the therapeutic medical device to heat coolant.

15. A cooling system for a therapeutic medical device, comprising:
  at least one heat exchanger made at least partially of plastic, the heat exchanger receiving coolant from the medical device and returning coolant thereto;
  a thermal electric cooler (TEC) in thermal contact with the heat exchanger for removing heat from the heat exchanger; and
  at least first and second heat exchangers in series.

16. The system of claim 15, further comprising first and second TEC assemblies, wherein each heat exchanger is associated with a respective TEC assembly.

17. The system of claim 15, further comprising at least one thermal barrier between the elements.

18. The system of claim 1, further comprising pump means communicating with the coolant for moving the coolant.

19. A cooling system, comprising:
  catheter means for conveying coolant into a patient's body without directly contacting the coolant with the body;
  heat exchanger means communicating with the catheter means for receiving therefrom and returning thereto coolant;
  cooling means in thermal contact with the heat exchanger means for conveying heat away from the heat exchanger means; and
  at least first and second heat exchanger means in fluid series with each other and first and second cooling means associated with the first and second heat exchanger means.

* * * * *